US 6,532,389 B1

(12) United States Patent
Shahandeh

(10) Patent No.: US 6,532,389 B1
(45) Date of Patent: Mar. 11, 2003

(54) IMPLANTABLE MEDICAL DEVICE WITH SINGLE BIT UPSET ERROR DETECTION AND CORRECTION

(75) Inventor: Reza Shahandeh, Westlake Village, CA (US)

(73) Assignee: Pacesetter, Inc., Sylmar, CA (US)

( * ) Notice: Subject to any disclaimer, the term of this patent is extended or adjusted under 35 U.S.C. 154(b) by 10 days.

(21) Appl. No.: 09/931,482

(22) Filed: Aug. 15, 2001

Related U.S. Application Data

(63) Continuation of application No. 09/877,441, filed on Jun. 8, 2001.

(51) Int. Cl.[7] .............................................. A61N 1/362
(52) U.S. Cl. ......................................................... 607/27
(58) Field of Search ........................... 607/4–9, 27, 31; 714/1–57, 699–824

(56) References Cited

U.S. PATENT DOCUMENTS

| | | |
|---|---|---|
| 4,712,555 A | 12/1987 | Thornander et al. |
| 4,788,980 A | 12/1988 | Mann et al. |
| 4,940,052 A | 7/1990 | Mann et al. |
| 4,944,298 A | 7/1990 | Sholder |
| 5,466,254 A | 11/1995 | Helland ........................ 607/123 |
| 6,128,528 A | * 10/2000 | Ericksen et al. |
| H1915 H | * 11/2000 | Boone et al. |

* cited by examiner

Primary Examiner—Scott M. Getzow

(57) ABSTRACT

Byte-based and page-based techniques for performing error detection and correction in an implantable medical device with minimal overhead are provided. With the byte-based technique, single bit upset errors are detected by hardware during a read cycle. A software-based error correction system corrects single bit errors and detects multi-bit errors. By providing error detection in hardware and error correction in software, single bit errors can be immediately detected during read cycles such that a microcontroller of the implantable device is not at risk of receiving erroneous data. Yet the total error detection and correction overhead is kept low so that the size, cost, and longevity of the implantable device are not significantly and adversely affected. With the page-based technique, single bit upset errors are detected and corrected by software between therapy delivery cycles, such as between successive pacing cycles. By providing error detection and correction between therapy delivery cycles, single bit errors can be detected before therapy is administered such that inappropriate therapy is avoided. The total error detection and correction overhead of the page-based technique is even less than with the byte-based technique.

19 Claims, 6 Drawing Sheets

FIG. 5

| | _0 | _1 | _2 | _3 | _4 | _5 | _6 | _7 | |
|---|---|---|---|---|---|---|---|---|---|
| D0 | D0_0 | D0_1 | D0_2 | D0_3 | D0_4 | D0_5 | D0_6 | D0_7 | P0 |
| D1 | D1_0 | D1_1 | D1_2 | D1_3 | D1_4 | D1_5 | D1_6 | D1_7 | P1 |
| D2 | D2_0 | D2_1 | D2_2 | D2_3 | D2_4 | D2_5 | D2_6 | D2_7 | P2 |
| D3 | D3_0 | D3_1 | D3_2 | D3_3 | D3_4 | D3_5 | D3_6 | D3_7 | P3 |
| ⋮ | | | | | | | | | |
| DN−1 | DN−1_0 | DN−1_1 | DN−1_2 | DN−1_3 | DN−1_4 | DN−1_5 | DN−1_6 | DN−1_7 | PN−1 |
| CP | CP_0 | CP_1 | CP_2 | CP_3 | CP_4 | CP_5 | CP_6 | CP_7 | CP-P |

| D0_0 | --- | --- | --- | --- | --- | D0_6 | D0_7 | --- | D127_1 | --- | D127_0 | P0 |
|---|---|---|---|---|---|---|---|---|---|---|---|---|
| D128_0 | --- | --- | --- | --- | --- | D128_6 | D128_7 | --- | D255_1 | --- | D255_0 | P1 |
| D256_0 | --- | --- | --- | --- | --- | D256_6 | D256_7 | --- | D383_1 | --- | D383_0 | P2 |
| D384_0 | --- | --- | --- | --- | --- | D384_6 | D384_7 | --- | D511_1 | --- | D511_0 | P3 |
| | | | | | | | | | | | | |
| D(N−1)*128_0 | --- | --- | --- | --- | --- | D(N−1)*128_6 | D(N−1)*128_7 | --- | D(N−1)*128+127_1 | --- | D(N−1)*128+127_0 | PN−1 |
| CP1_0 | --- | --- | --- | --- | --- | CP1_6 | CP1_7 | --- | CP128_7 | --- | CP128_0 | CP-P |

301

IMPLANTABLE MEDICAL DEVICE WITH SINGLE BIT UPSET ERROR DETECTION AND CORRECTION

FIELD OF THE INVENTION

The invention generally relates to implantable medical devices and in particular to error detection and correction techniques for use within such devices.

BACKGROUND OF THE INVENTION

A wide variety of implantable medical devices are provided for surgical implantation into humans or animals. One common example is the cardiac pacemaker. Another is the implantable cardioverter defibrillator (ICD). State of the art implantable medical devices often include a programmable microcontroller for controlling the functions of the device to detect medical conditions within the patient in which the device is implanted and to control delivery of appropriate therapy. Within a pacemaker, for example, the microcontroller monitors the detection of P-waves and R-waves within electrical heart signals to determine whether an episode of bradycardia has occurred and, if so, controls a pulse generator to generate pacing pulses for delivery to the heart. Within an ICD, for example, the microcontroller analyzes P-waves, R-waves and other electrical signals of the heart to determine if an episode of ventricular fibrillation has occurred and, if so, controls a shocking circuit to generate a defibrillation shock for delivery to the heart. In addition to performing functions directed to deliver of therapy, the microcontroller coordinates all other functions of the implantable device such as: monitoring a battery of the device to determine if the battery needs to be replaced; switching of the mode of operation of the device from, for example, a single-chambered pacing mode to a dual-chambered pacing mode; and recording events such as detection of P-waves and R-waves for diagnostic purposes.

The microcontroller operates using control software and data stored in a memory system of the implantable device. The control software specifies the operations to be performed by the microcontroller. The control data provides parameters for controlling the software, such as parameters specifying the amount of electrical energy to employ for pacing pulses or defibrillation shocks or specifying whether the device is to operate in a dual-chamber or a single-chamber mode. The memory system also stores diagnostic information for subsequent transmission to an external programmer device for review by physicians or other personnel. The diagnostic information may include patient diagnostic data such as digitized recordings of internal electrogram (IEGM) signals and device diagnostic data such as measured battery voltages, lead impedances, and the like. Data stored in the memory system, including the control software, is stored in binary form, i.e. the data is stored as sequences of bits comprising ones or zeros. State of the art devices have memory systems storing one megabyte or more of binary data wherein a byte comprises eight bits of binary data.

Significant problems can arise if an error occurs in the control software or other data stored within the memory system. Errors can occur, for example, as a result of alpha particles striking the memory or as a result of atmospheric neutron flux, either of which can cause one or more of the individual binary values stored in the memory system to flip from a one to zero or vice versa. If the error occurs in the portion of the memory storing control software, the microcontroller might no longer be able to operate correctly and, as a result, might administer therapy when none is required or fail to administer therapy when it is required. In some cases, an error in the control software might prevent the microcontroller from operating at all, resulting in a complete lack of therapy. If the error occurs in the portion of the memory storing the control parameters, the microcontroller will likely continue to operate but might implement an incorrect mode of operation (such as performing single-chamber pacing instead of dual-chamber pacing) or might apply too much or too little electrical energy in pacing or defibrillation pulses. Errors occurring in the portion of the memory storing diagnostic information can result in a subsequent misdiagnosis of medical conditions within the patient by a physician reviewing the data or can result in a failure to properly determine when batteries or leads of the implanted device need to be replaced.

As can be appreciated, there is a significant need to provide reliable error detection and correction techniques for automatically detecting and correcting errors occurring within the memory system to ensure that the microcontroller performs the correct functions using the correct control parameters and stores the correct diagnostic data. Preferably, errors are detected and corrected promptly to ensure that the errors do not affect the delivery of therapy. Ideally, an error detection and correction system is provided that can examine data as it is read from memory to immediately detect and correct any errors found therein such that the microcontroller is never at risk of receiving erroneous data. Also, ideally, the error detection and correction system is capable of detecting and correcting either single bit or multiple bit errors. However, to achieve immediate detection and correction of single- or multiple-bit errors, the error detection and correction system typically needs to be implemented entirely in hardware to ensure quick operation and typically must devote a large percentage of the total memory space to error detection and correction bits. To this end, an error detection and correction system could be provided employing five error detection and correction bits for each eight-bit byte of actual data. By providing five error detection and correction bits per byte, single or multiple-bit errors can be detected and corrected using hardware as the data is read. However, the error detection and correction overhead necessitated by such as system is 62.5% (i.e. 13 total bits per byte/8 data bits per byte*100). In other words, fully 38.5% of the memory of the implantable device is devoted to error detection and correction bits and only 61.5% of the memory actually stores useable data, such as control software, control parameters, or diagnostic data. The many error detection and correction bits consume considerable circuit space within the implantable device and consume considerable power and thereby significantly and adversely affect the size, cost and longevity of the implantable device. Moreover, to provide the error detection and correction just described, the device would need to be designed and manufactured using thirteen-bit memory chips. Hence, implantable devices that have already been implanted cannot easily be upgraded to provide error detection and correction. For at least these reasons, error detection and correction systems of the type described are typically not implemented within implantable medical devices. Instead, some implantable devices perform only error detection, but no correction, or perform no error detection or correction whatsoever.

Accordingly, it would be highly desirable to provide an improved error detection and correction system for use within an implantable medical device, which achieves an adequate degree of error detection and correction with minimal overhead to thereby reduce the amount of memory space required to implement error detection and correction and to also reduce the amount of power consumed. It would also be highly desirable to provide an embodiment of the improved error detection and correction system that can be implemented entirely in software so that medical devices that have already been implanted can be upgraded to provide error detection and correction merely by loading new software into the device. It is to these ends that aspects of the invention are primarily directed.

SUMMARY OF THE INVENTION

In accordance with a first aspect of the invention, a hybrid hardware/software error detection and correction system is provided for performing error detection and correction within an implantable medical device. The implantable device includes a microcontroller for controlling operations of the device and a memory unit for storing control software and data for use by the microcontroller. The error detection and correction system includes a hardware-based error detection unit for performing a parity check on a row of the memory and a software-based single-bit error correction unit, responsive to the detection of a parity error in a row of the memory, for correcting a single bit error within the row.

In an exemplary embodiment of the first aspect of the invention the implantable device is a cardiac stimulation device for administering pacing therapy. The memory employs nine-bit random access memory (RAM) chips having a parity bit hardwired to each data-storage byte. Each byte represents one row of the memory. The error detection unit comprises hardwired circuitry within the memory chip for performing a parity check on each byte of data as the byte is read during a read cycle. Hence, single bit upset errors are detected immediately upon reading a byte containing an error. The error correction unit is implemented as a software module for correcting single bit errors using a set of column parity bits and a page parity bit, which are calculated and stored by the error correction unit in memory. By providing error detection in hardware and error correction in software, single bit errors can be immediately detected during read operations such that the microcontroller is not at risk of receiving data with single bit errors. Yet the total error detection and correction overhead is kept low so that the size, cost, and longevity of the implantable device are not significantly and adversely affected. For a 32 K-byte memory chip, the total parity bit overhead is only 13.28%— substantially less than the 62.5% overhead required by the conventional systems described above, which employ five parity bits for every eight bits of data. Since the overhead is low, error detection and correction can be provided within implantable devices that would not otherwise be able to accommodate conventional error detection and correction systems. Although multiple-bit errors cannot be corrected with this system, the error correction software can typically detect such errors, depending upon their location in memory, such that other appropriate remedial steps can be taken, such as switching to a backup therapy controller. In any case, the provision of single-bit error detection and correction represents a significant improvement over implantable medical devices that perform no error correction whatsoever.

In accordance with a second aspect of the invention, a software-based error detection and correction system is provided for performing error detection and correction of single-bit upset errors within an implantable medical device. The implantable device includes a microcontroller for controlling operations of the device, a memory unit for storing control software and data for use by the microcontroller, and the software-based error detection and correction system. The microcontroller controls operations of the device by identifying a sequence of successive therapy delivery cycles and administers therapy, if necessary, based on the cycles. The error detection and correction system operates between successive cycles to examine portions of memory to identify any single-bit errors therein. If an error is detected, the software-based error detection and correction system corrects the single-bit error before the next pacing cycle.

In an exemplary embodiment of the second aspect of the invention, the implantable device is a cardiac stimulation device for administering pacing therapy. The memory employs eight-bit RAM chips without hardwired parity bits. Each page of memory represents one row of a multi-page memory array. One page parity bit is stored for each page of the memory array. A set of column parity bytes and one array parity bit are stored for the entire memory array. The page, column, and array parity bits are calculated by the software-based error detection and correction system and are stored in memory. The error detection and correction system unit operates between pacing cycles to perform a parity check on each page of data in the array and to correct any single-bit upset errors therein. By providing error detection and correction between pacing cycles, single bit errors can be detected before therapy is administered such that inappropriate therapy is avoided. The total error detection and correction overhead is significantly less than that of the byte-based embodiment summarized above and dramatically less than conventional thirteen-bit systems. Indeed, for a 32 K-byte memory chip with a page size of 128 bytes, the total parity bit overhead is only 0.49%. Moreover, because error detection and correction is implemented with software, implantable devices that have already been implanted can be upgraded to incorporate error detection and correction, so long as sufficient memory space is available for the additional error detection and correction software. As with the byte-based system summarized above, multiple-bit errors typically can be detected but not corrected with this system.

Other objects and advantages of the invention are achieved as well. Method embodiments of the invention are also provided.

BRIEF DESCRIPTION OF THE DRAWINGS

Further features and advantages of the invention may be more readily understood by reference to the following description taken in conjunction with the accompanying drawings, in which:

FIG. 5 illustrates a page of memory processed by the byte-based error detection and correction method of FIGS. 3–4;

FIG. 8 illustrates a multi-page memory array processed by the page-based error detection and correction method of FIGS. 3–4.

DETAILED DESCRIPTION OF THE PREFERRED EMBODIMENTS

The following description is of the best mode presently contemplated for practicing the invention. The description is not to be taken in a limiting sense but is provided merely for the purpose of describing the general principles of the invention. The scope of the invention should be ascertained with reference to the issued claims. In the description of exemplary embodiments of the invention that follows, like numerals or reference designators will be used to refer to like parts or elements throughout.

Overview of Implantable Medical Device

Figure 1:
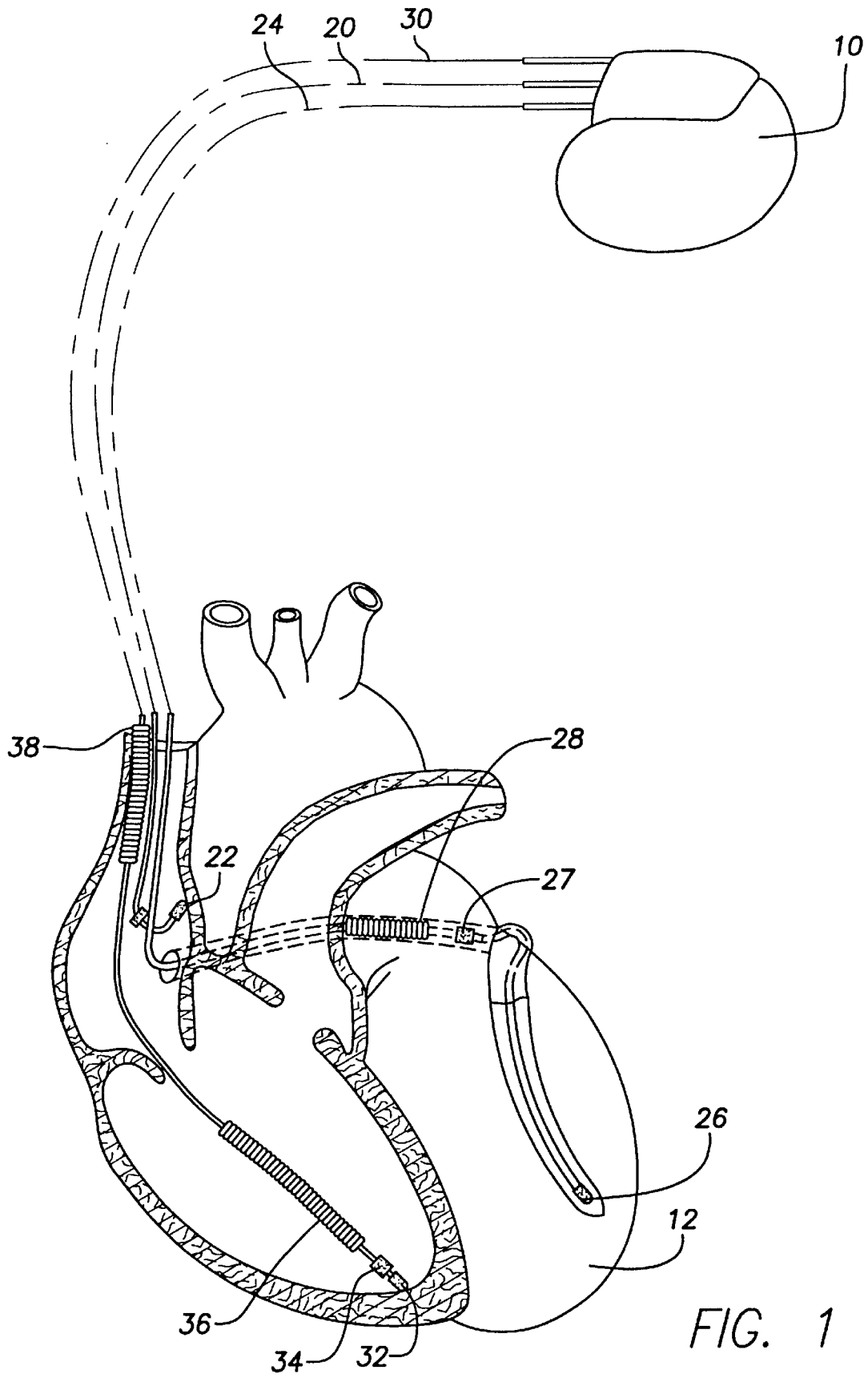
FIG. 1 is a simplified diagram illustrating an implantable cardiac stimulation device in electrical communication with at least three leads implanted into a patient's heart for delivering multi-chamber stimulation and shock therapy.

As shown in FIG. 1, there is a stimulation device 10 in electrical communication with a patient's heart 12 by way of three leads, 20, 24 and 30, suitable for delivering multi-chamber stimulation and shock therapy. To sense atrial cardiac signals and to provide right atrial chamber stimulation therapy, the stimulation device 10 is coupled to an implantable right atrial lead 20 having at least an atrial tip electrode 22, which typically is implanted in the patient's right atrial appendage.

To sense left atrial and ventricular cardiac signals and to provide left chamber pacing therapy, the stimulation device 10 is coupled to a "coronary sinus" lead 24 designed for placement in the "coronary sinus region" via the coronary sinus os for positioning a distal electrode adjacent to the left ventricle and/or additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus.

Accordingly, an exemplary coronary sinus lead 24 is designed to receive atrial and ventricular cardiac signals and to deliver left ventricular pacing therapy using at least a left ventricular tip electrode 26, left atrial pacing therapy using at least a left atrial ring electrode 27, and shocking therapy using at least a left atrial coil electrode 28. For a complete description of a coronary sinus lead, see U.S. Pat. No. 5,466,254, "Coronary Sinus Lead with Atrial Sensing Capability" (Helland), which patents are hereby incorporated herein by reference.

The stimulation device 10 is also shown in electrical communication with the patient's heart 12 by way of an implantable right ventricular lead 30 having, in this embodiment, a right ventricular tip electrode 32, a right ventricular ring electrode 34, a right ventricular (RV) coil electrode 36, and an SVC coil electrode 38. Typically, the right ventricular lead 30 is transvenously inserted into the heart 12 so as to place the right ventricular tip electrode 32 in the right ventricular apex so that the RV coil electrode will be positioned in the right ventricle and the SVC coil electrode 38 will be positioned in the superior vena cava. Accordingly, the right ventricular lead 30 is capable of receiving cardiac signals, and delivering stimulation in the form of pacing and shock therapy to the right ventricle.

Figure 2:
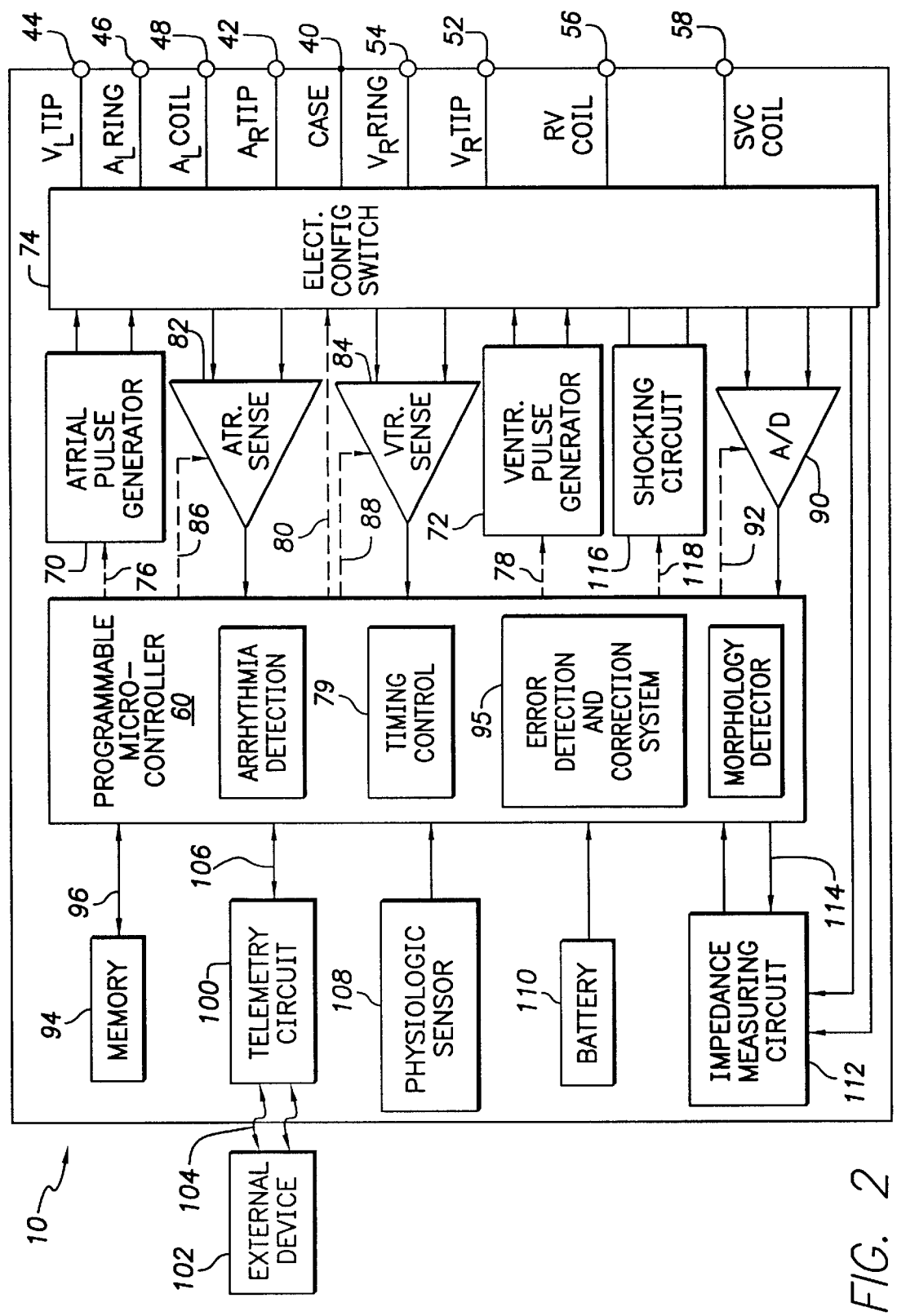
FIG. 2 is a functional block diagram of a multi-chamber implantable stimulation device illustrating the basic elements of a stimulation device, which can provide cardioversion, defibrillation and pacing stimulation in four chambers of the heart.

As illustrated in FIG. 2, a simplified block diagram is shown of the multi-chamber implantable stimulation device 10, which is capable of treating both fast and slow arrhythmias with stimulation therapy, including cardioversion, defibrillation, and pacing stimulation. While a particular multi-chamber device is shown, this is for illustration purposes only, and one of skill in the art could readily duplicate, eliminate or disable the appropriate circuitry in any desired combination to provide a device capable of treating the appropriate chamber(s) with cardioversion, defibrillation and pacing stimulation.

The housing 40 for the stimulation device 10, shown schematically in FIG. 2, is often referred to as the "can", "case" or "case electrode" and may be programmably selected to act as the return electrode for all "unipolar" modes. The housing 40 may further be used as a return electrode alone or in combination with one or more of the coil electrodes, 28, 36 and 38, for shocking purposes. The housing 40 further includes a connector (not shown) having a plurality of terminals, 42, 44, 46, 48, 52, 54, 56, and 58 (shown schematically and, for convenience, the names of the electrodes to which they are connected are shown next to the terminals). As such, to achieve right atrial sensing and pacing, the connector includes at least a right atrial tip terminal ($A_R$ TIP) 42 adapted for connection to the atrial tip electrode 22.

To achieve left chamber sensing, pacing and shocking, the connector includes at least a left ventricular tip terminal ($V_L$ TIP) 44, a left atrial ring terminal ($A_L$ RING) 46, and a left atrial shocking terminal ($A_L$ COIL) 48, which are adapted for connection to the left ventricular ring electrode 26, the left atrial tip electrode 27, and the left atrial coil electrode 28, respectively.

To support right chamber sensing, pacing and shocking, the connector further includes a right ventricular tip terminal ($V_R$ TIP) 52, a right ventricular ring terminal ($V_R$ RING) 54, a right ventricular shocking terminal ($R_V$ COIL) 56, and an SVC shocking terminal (SVC COIL) 58, which are adapted for connection to the right ventricular tip electrode 32, right ventricular ring electrode 34, the RV coil electrode 36, and the SVC coil electrode 38, respectively.

At the core of the stimulation device 10 is a programmable microcontroller 60, which controls the various modes of stimulation therapy. As is well known in the art, the microcontroller 60 typically includes a microprocessor, or equivalent control circuitry, designed specifically for controlling the delivery of stimulation therapy and may further include RAM or ROM memory, logic and timing circuitry, state machine circuitry, and I/O circuitry. Typically, the microcontroller 60 includes the ability to process or monitor input signals (data) as controlled by a program code stored in a designated block of memory. The details of the design and operation of the microcontroller 60 are not critical to the present invention. Rather, any suitable microcontroller 60 may be used that carries out the functions described herein. The use of microprocessor-based control circuits for performing timing and data analysis functions are well known in the art.

Representative types of control circuitry that may be used with the invention include the microprocessor-based control system of U.S. Pat. No. 4,940,052 (Mann et al.), the state-machine of U.S. Pat. Nos. 4,712,555 (Sholder) and 4,944,298 (Sholder). For a more detailed description of the various timing intervals used within the stimulation device and their inter-relationship, see U.S. Pat. No. 4,788,980 (Mann et al.). The '052, '555, '298 and '980 patents are incorporated herein by reference.

As shown in FIG. 2, an atrial pulse generator 70 and a ventricular pulse generator 72 generate pacing stimulation pulses for delivery by the right atrial lead 20, the right ventricular lead 30, and/or the coronary sinus lead 24 via an electrode configuration switch 74. It is understood that in order to provide stimulation therapy in each of the four chambers of the heart, the atrial and ventricular pulse generators, 70 and 72, may include dedicated, independent pulse generators, multiplexed pulse generators, or shared pulse generators. The pulse generators, 70 and 72, are controlled by the microcontroller 60 via appropriate control signals, 76 and 78, respectively, to trigger or inhibit the stimulation pulses.

The microcontroller 60 further includes timing control circuitry 79 which is used to control the timing of such stimulation pulses (e.g., pacing rate, atrio-ventricular (AV) delay, atrial interconduction (A—A) delay, or ventricular interconduction (V—V) delay, etc.) as well as to keep track of the timing of refractory periods, blanking intervals, noise detection windows, evoked response windows, alert intervals, marker channel timing, etc., which is well known in the art.

The switch 74 includes a plurality of switches for connecting the desired electrodes to the appropriate I/O circuits, thereby providing complete electrode programmability. Accordingly, the switch 74, in response to a control signal 80 from the microcontroller 60, determines the polarity of the stimulation pulses (e.g., unipolar, bipolar, combipolar, etc.) by selectively closing the appropriate combination of switches (not shown) as is known in the art.

Atrial sensing circuits 82 and ventricular sensing circuits 84 may also be selectively coupled to the right atrial lead 20, coronary sinus lead 24, and the right ventricular lead 30, through the switch 74 for detecting the presence of cardiac activity in each of the four chambers of the heart. Accordingly, the atrial (ATR. SENSE) and ventricular (VTR. SENSE) sensing circuits, 82 and 84, may include dedicated sense amplifiers, multiplexed amplifiers, or shared amplifiers. The switch 74 determines the "sensing polarity" of the cardiac signal by selectively closing the appropriate switches, as is also known in the art. In this way, the clinician may program the sensing polarity independent of the stimulation polarity.

Each sensing circuit, 82 and 84, preferably employs one or more low power, precision amplifiers with programmable gain and/or automatic gain control, bandpass filtering, and a threshold detection circuit, as known in the art, to selectively sense the cardiac signal of interest. The automatic gain control enables the device 10 to deal effectively with the difficult problem of sensing the low amplitude signal characteristics of atrial or ventricular fibrillation. The outputs of the atrial and ventricular sensing circuits, 82 and 84, are connected to the microcontroller 60 which, in turn, are able to trigger or inhibit the atrial and ventricular pulse generators, 70 and 72, respectively, in a demand fashion in response to the absence or presence of cardiac activity in the appropriate chambers of the heart. For arrhythmia detection, the device 10 utilizes the atrial and ventricular sensing circuits, 82 and 84, to sense cardiac signals to determine whether a rhythm is physiologic or pathologic. As used herein "sensing" is reserved for the noting of an electrical signal, and "detection" is the processing of these sensed signals and noting the presence of an arrhythmia. The timing intervals between sensed events (e.g., P-waves, R-waves, and depolarization signals associated with fibrillation which are sometimes referred to as "F-waves" or "Fib-waves") are then classified by the microcontroller 60 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, anti-tachycardia pacing, cardioversion shocks or defibrillation shocks, collectively referred to as "tiered therapy").

Cardiac signals are also applied to the inputs of an analog-to-digital (A/D) data acquisition system 90. The data acquisition system 90 is configured to acquire intracardiac electrogram signals, convert the raw analog data into a digital signal, and store the digital signals for later processing and/or telemetric transmission to an external device 102. The data acquisition system 90 is coupled to the right atrial lead 20, the coronary sinus lead 24, and the right ventricular lead 30 through the switch 74 to sample cardiac signals across any pair of desired electrodes.

The microcontroller 60 is further coupled to a memory 94 by a suitable data/address bus 96, wherein the programmable operating parameters used by the microcontroller 60 are stored and modified, as required, in order to customize the operation of the stimulation device 10 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart 12 within each respective tier of therapy.

The microcontroller includes an error detection and correction system 95 for detecting and correcting single bit errors occurring in memory 94. In one embodiment described below, memory 94 is nine-bit RAM provided with circuitry for detecting parity errors as data is read from the memory by the microcontroller. The error detection and correction system of the microcontroller is a software module that processes parity error signals received from the memory to correct single bit errors. In another embodiment also described below, memory 94 is eight-bit RAM that is not hardwired to detect parity errors. The error detection and correction system of the microcontroller handles detects parity errors as well as handling the correction of the errors. In both embodiments, various parity errors bits are calculated by the error detection and correction system for storage in the memory along with data.

Advantageously, the operating parameters of the implantable device 10 may be non-invasively programmed into the memory 94 through a telemetry circuit 100 in telemetric communication with the external device 102, such as a programmer, transtelephonic transceiver, or a diagnostic system analyzer. The telemetry circuit 100 is activated by the microcontroller by a control signal 106. The telemetry circuit 100 advantageously allows intracardiac electrograms and status information relating to the operation of the device 10 (as contained in the microcontroller 60 or memory 94) to be sent to the external device 102 through an established communication link 104.

In the preferred embodiment, the stimulation device 10 further includes a physiologic sensor 108, commonly referred to as a "rate-responsive" sensor because it is typically used to adjust pacing stimulation rate according to the exercise state of the patient. However, the physiological sensor 108 may further be used to detect changes in cardiac output, changes in the physiological condition of the heart, or diurnal changes in activity (e.g., detecting sleep and wake states). Accordingly, the microcontroller 60 responds by adjusting the various pacing parameters (such as rate, AV Delay, V—V Delay, etc.) at which the atrial and ventricular pulse generators, 70 and 72, generate stimulation pulses. The type of sensor used is not critical to the invention and is shown only for completeness.

The stimulation device additionally includes a battery 110 that provides operating power to all of the circuits shown in FIG. 2. For the stimulation device 10, which employs shocking therapy, the battery 110 must be capable of operating at low current drains for long periods of time, and then be capable of providing high-current pulses (for capacitor charging) when the patient requires a shock pulse. The battery 110 must also have a predictable discharge characteristic so that elective replacement time can be detected. Accordingly, the device 10 preferably employs lithium/silver vanadium oxide batteries, as is true for most (if not all) current devices. As further shown in FIG. 2, the device 10 is shown as having an impedance measuring circuit 112 which is enabled by the microcontroller 60 via a control signal 114.

In the case where the stimulation device 10 is intended to operate as an implantable cardioverter/defibrillator (ICD) device, it must detect the occurrence of an arrhythmia, and automatically apply an appropriate electrical shock therapy to the heart aimed at terminating the detected arrhythmia. To this end, the microcontroller 60 further controls a shocking circuit 116 by way of a control signal 118. The shocking circuit 116 generates shocking pulses of low (up to 0.5 Joules), moderate (0.5–10 Joules), or high energy (11 to 40 Joules), as controlled by the microcontroller 60. Such shocking pulses are applied to the patient's heart 12 through at least two shocking electrodes, and as shown in this embodiment, selected from the left atrial coil electrode 28, the RV coil electrode 36, and/or the SVC coil electrode 38. As noted above, the housing 40 may act as an active electrode in combination with the RV electrode 36, or as part of a split electrical vector using the SVC coil electrode 38 or the left atrial coil electrode 28 (i.e., using the RV electrode as a common electrode).

Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 5–40 Joules), delivered asynchronously (since R-waves may be too disorganized), and pertaining exclusively to the treatment of fibrillation. Accordingly, the microcontroller 60 is capable of controlling the synchronous or asynchronous delivery of the shocking pulses.

Figure 3:
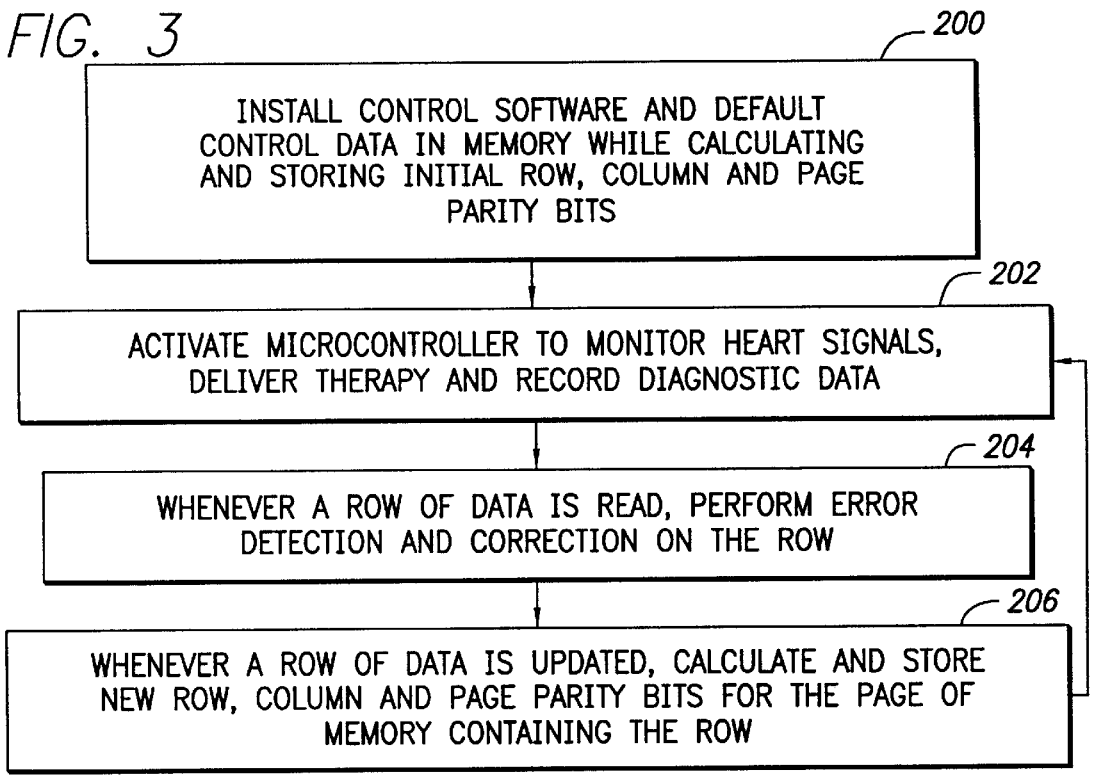
FIG. 3 is a flow chart providing an overview of a byte-based method for performing error detection and correction within the implantable device of FIGS. 1 and 2 in accordance with a first aspect of the invention.
Figure 4:
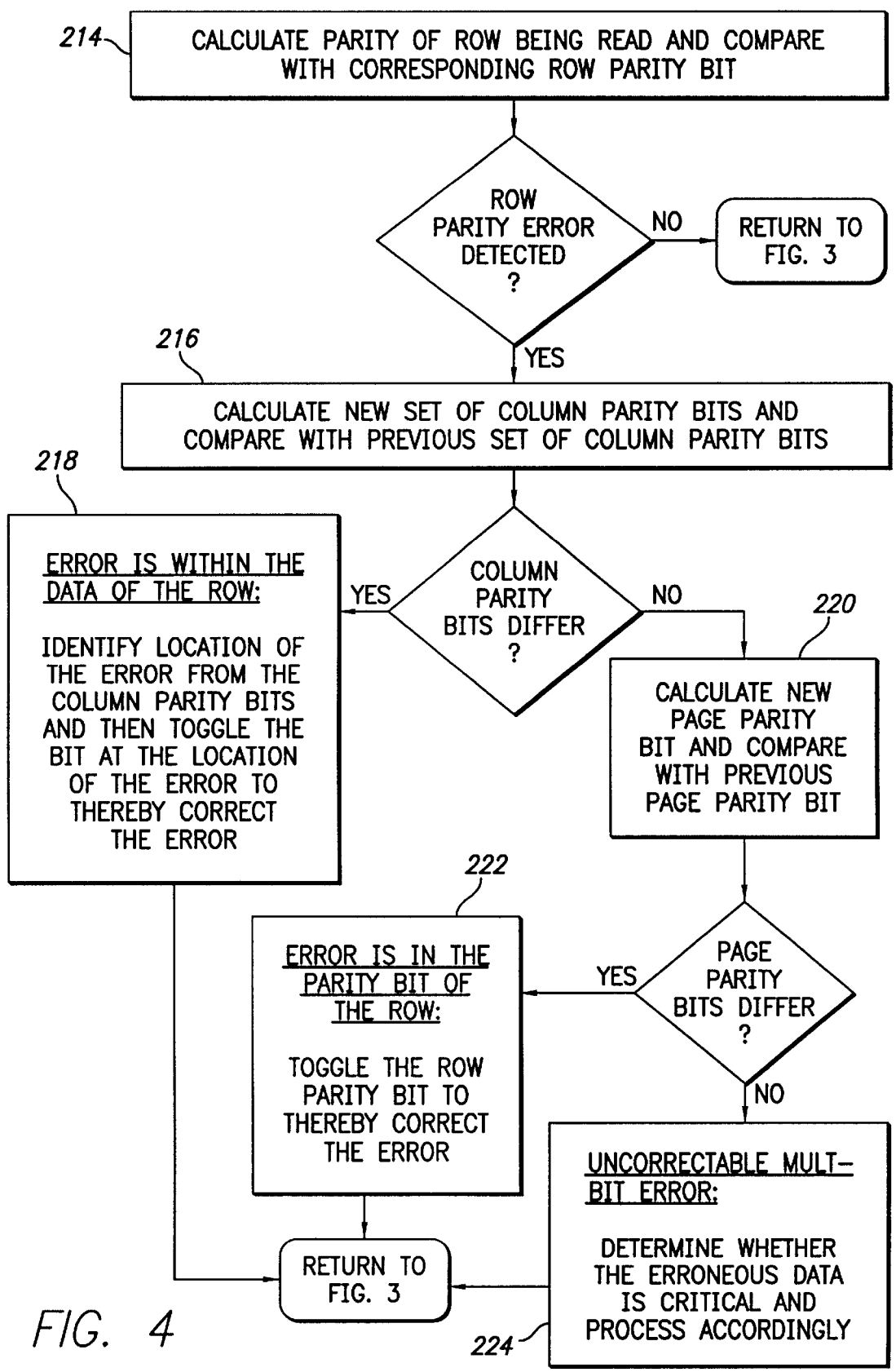
FIG. 4 is a flow chart illustrating details of the byte-based error detection and correction method of FIG. 3.

Byte-based Error Detection and Correction Method Using Hybrid Hardware/Software System FIGS. 3 and 4 are flow charts providing an overview of the operation and novel features implemented in a first embodiment of device 10. In the flow charts, and other flow charts described herein, the various algorithmic steps are summarized in individual "blocks". Such blocks describe specific actions or decisions that must be made or carried out as the algorithm proceeds. Where a microcontroller (or equivalent) is employed, the flow charts presented herein provide the basis for a "control program" that may be used by such a microcontroller (or equivalent) to effectuate the desired control of the stimulation device. Those skilled in the art may readily write such a control program based on the flow charts and other descriptions presented herein.

Initially, at step 200, control software and initial control data is installed into the memory of the device. As the software and data is written to memory, memory 94 (FIG. 2) calculates and stores row parity bits associated with each row of the memory and the error detection and correction system 95 (also FIG. 2) calculates and stores column parity bits for each column of each page of the memory. The error detection and correction system also calculates a stores a single page parity bit for each page of the memory.

FIG. 5 illustrates an example of one page 201 of 9-bit memory having N single-byte rows with eight data bits per row and one parity bit per row. N is 128 for a 128-byte page of memory and 256 for a 256-byte page of memory. Numerous memory chips may be employed, each having numerous pages, yielding a total memory space of perhaps one megabyte or more. For each page, eight column parity bits (CP_0 through CP_7) and N row parity bits (P_0 through P_N) are calculated and stored. Row parity bit P0 is generated based on the eight data bits of row 0 of the RAM; row parity bit P1 is generated based on the eight data bits of row 1 of the RAM; and so on with row parity bit PN−1 generated based on the eight data bits of the last row of the RAM (row N−1). Column parity bit CP0 is generated based on the N data bits of column 0 of the RAM; column parity bit CP1 is generated based on the N data bits of column 1 of the RAM; and so on with column parity bit CP7 generated based on the N data bits of the column 7 of the RAM. A page parity bit CP_P is generated based on the eight column parity bits. The column parity byte and page parity bit are stored in additional RAM space; therefore, for every 256 bytes of RAM, two additional bytes are required to store the column and page parity bits. For a 32K RAM, 256 bytes (32K-bytes/256 bytes)*2) are required for the column and page parity bits yielding an overhead of 0.78% (256 bytes/32 K-bytes*100). The row parity bits require 12.5% of overhead (9 bits total/8 bits of data* 100). The total parity bit overhead is therefore 13.28%. This is substantially less than the 62.5% overhead required by the conventional systems described above, which employ five parity bits for every eight bits of data.

Preferably, the memory is configured to calculate and store the row parity bits using hardwired circuitry whenever data is written to the memory. For a portion of memory storing control software, the data is typically written only when the control software is initially loaded into the implantable device at the factory or when an external programmer updates the control software. For a portion of memory storing control parameters or diagnostic data, the data may be re-written frequently, perhaps once every pacing cycle. In any case, by providing hardwired circuitry for calculating and storing row parity bits whenever data is written to the memory, the row parity bits are always up to date. The column parity bits and the page parity bit are calculated by the error detection and correction system and stored separately from the memory.

Beginning at step 202, the microcontroller is activated to begin processing electrical heart signals and other information in an attempt to determine whether pacing therapy, or any other form of therapy, is required. To this end, the microcontroller processes signals representative of intrinsic events such as P-waves, R-waves, T-waves and the like and, if needed, delivers pacing pulses in the form of A-pulses or V-pulses. Diagnostic data, such as recordings of IEGM signals, are stored in the memory by the microcontroller. While performing these functions, the microcontroller frequently access the memory to either read data therefrom (such as control parameters) or to update data already stored (such as to record new diagnostic data such as new IEGM signals.) Whenever data is read from memory, at step 204, error detection and correction is automatically performed on each row of memory being read. Whenever data is written to the memory, at step 206, new row, column, and page parity bits are calculate and stored. The row parity bits are calculated and stored by the circuitry of the RAM. The column and page parity bits are calculated and stored by the error detection and correction system.

Referring now to FIG. 4, the error detection and correction process performed whenever data is read from a row of memory at step 204 of FIG. 3 will now be described. At step 214, the parity of the row being read is compared with the previous row parity by circuitry of the RAM. If the new row parity bit matches the previous row parity bit, then a single bit error has not occurred in the row and processing returns to FIG. 3. If, however, the new row parity bit does not match the stored row parity bit for the row being read, then an error has occurred and a parity error signal is sent by the RAM to the error detection and correction system, which at step 216 calculates a new set of column parity bits and compares the new column parity bits with the previous column parity bits. If the new column parity bits differ from the previous column parity bits, then a single bit error has occurred in the data of the row and step 218 is performed to correct the error. The error is corrected by identifying the specific column parity bit that differs, then toggling the corresponding data bit of the row. In the example of FIG. 5, if new column parity bit C__3 differs from stored column parity bit C__3 for the byte of row 1 of the memory, the error is therefore located at bit D1__3 and that bit is switched, i.e. if the bit is currently set to a 1, it is switched to a 0 and vice versa. Actual correction is preferably achieved by reading the entire erroneous byte from memory, then XORing the erroneous byte with the new column parity byte to thereby correct the error (i.e. by performing an exclusive OR logic operation on the erroneous byte and the new column parity byte). The error is thus corrected and processing returns to FIG. 3.

If following step 216, the new column parity bits do not differ from the stored column parity bits, then either the error is in the row parity bit itself or a multiple bit error has occurred that cannot be corrected. To determine whether the row parity bit is in error, at step 220, a new page parity bit is calculated based on the new column parity bits and is compared against the initial page parity bit. If the page parity bits differ, the error is in the row parity bit. In the example of FIG. 5, if new page parity bit CP__P differs from stored page parity bit CP__P based on an error initially detected in the fourth row, the error is therefore at bit P3 and that bit is switched, i.e. if the bit is currently set to a 1, it is switched to a 0 and vice versa. Actual correction is preferably achieved at step 222 by re-writing the byte of the corrupted row, thereby triggering the hardware to automatically calculate and store a new row parity bit. Processing then returns to FIG. 3.

Following step 220, if the new page parity bit matches the stored page parity bit, then an uncorrectable multiple-bit error has occurred. In the example of FIG. 5, if an error has occurred both at bit location number 3 within row 1 and at bit location number 2 within row 5, the new and old column parity bytes will match and the new and old page parity bit will also match. In this case, it is not possible for the system to locate the two errors. At step 224, the system determines whether the data stored within the tested portion of memory is critical or not. Critical data may include, for example, control software. Non-critical data may include, for example, diagnostic data. If not critical, the error may either be simply ignored or the data discarded. For example, if the erroneous data is IEGM data, the error may simply be ignored. Typically, thousands of bytes of IEGM data are stored and an error in one bit of the IEGM data will likely be substantially insignificant. If the error, however, is within control software, the error may prevent proper administration of therapy. If a backup therapy delivery control system is provided, the backup system is activated to ensure that minimal therapy is delivered. If no backup system is provided, other appropriate steps are taken, such as generation of a warning alarm to the patient to alert the patient that the device may not be operating correctly so that the patient can immediately see a physician to have the control software re-installed.

In the following, a more detailed description of the error detection and correction techniques used in connection with the nine-bit RAM memory of FIG. 5 are provided. During each read cycle, hardware of the memory XORs the eight bits of data being read and compares the result with the row parity bit. Upon detection of a parity error, the hardware stores the address (m) where the parity error occurred. Software of the error detection and correction system then reads the contents of the entire page covering the faulty address and XORs all bytes of the page to generate an error column parity byte then XORs the eight bits of the error column parity byte to yield an error page parity bit. The error column parity byte and the stored column parity byte (CP__0–CP__7) are XORed to generate an error bit position byte. The error bit position byte is then XORed with the contents of the faulty address (Dm__7–Dm__0) to correct the error. However, if the error bit position byte is zero, then the software compares the error page parity bit with the stored page parity bit (CP__P). If they are different, the fault is in the parity bit of the faulty row (m) and is corrected by reading the data byte from the faulty address then re-writing the data to the address to thereby trigger the hardware to generate a new (correct) row parity bit. If the stored and calculated column parity bits are the same, a multiple bit error has occurred which is not correctable.

As a specific example of a single bit error correction, consider a case wherein the faulty address is at N=24 and the correct data is 11001010 with odd parity (i.e. the row parity bit is 1). The column parity byte is 10100101. If a single bit error occurs at bit position 5 (changing the data word to 11101010 with parity staying at 1), the next time address 24 is read, the hardware of the memory automatically detects the parity error. The software of the error detection and correction system then calculates the column parity byte as 10000101. After XORing the calculated and stored byte together, the result is 00100000, indicating bit position 5 as the erroneous bit. By XORing the result with the current data at address 24 (11101010 XOR 00100000=11001010), the data byte in address 24 is corrected to its original value.

As another example of a single bit error correction, consider another case wherein the faulty address is 24, the correct data is 11001010 with odd parity and the column parity byte is 10100101. If a single bit error occurs in the parity bit position (not changing the data word but changing the parity to 0), the next time address 24 is read, the hardware of the memory automatically detects the parity error. The software of the error detection ad correction system calculates the column parity byte as 10100101. After XORing the calculated and stored byte, the result is 00000000, indicating no erroneous bit. The software then calculates the parity for the column parity bits, which differ from the stored value. By re-writing the data word at address 24 (11001010) the parity bit is automatically re-calculated by hardware as 1 and the error is thereby corrected.

What has been described thus far is a byte-based error detection and correction system wherein every byte of data has a corresponding parity bit. As noted, substantially less overhead is required then with many conventional error detection and correction systems. In the following, a page-based error detection and correction system is described wherein only one row parity bit is required for each page of data. Even less overhead is thereby required. However, an advantage of the byte-based method over the page-based method is that errors are immediately detected upon reading the faulty address.

Page-Based Error Detection and Correction Method Using Software

Figure 6:
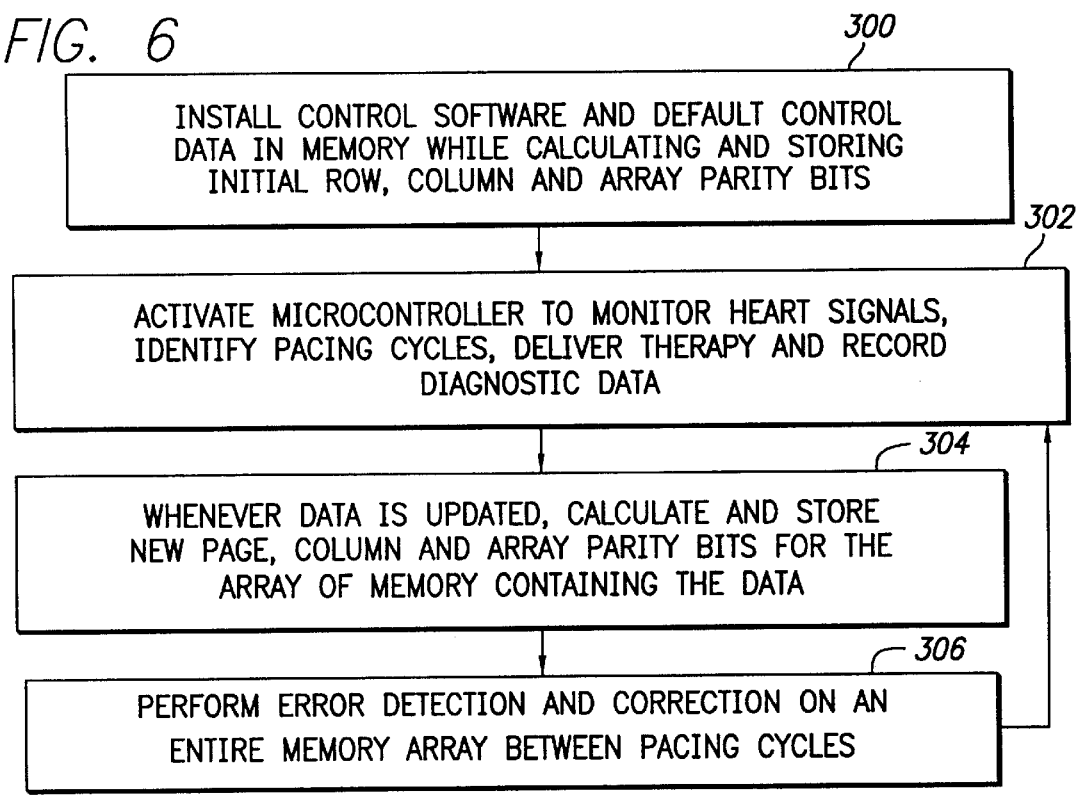
FIG. 6 is a flow chart providing an overview of a page-based method for performing error detection and correction within the implantable device of FIGS. 1 and 2 in accordance with a second aspect of the invention.

Within FIG. 6, at step 300, control software and default control data is initially installed into the memory of the device. As the software and data is written to the memory, error detection and correction system 95 (FIG. 2) calculates and stores initial row and column parity bits for each row and column of each page of the memory. The error detection and correction system also calculates a stores a single array parity bit for the entire memory array. A conventional 8-bit RAM is employed with no hardwired parity bits. Since the parity bits are not hardwired to the data bits, parity errors are not detected on each read cycle. Rather, as will be explained, error detection is periodically performed on an entire page of memory.

FIG. 8 illustrates an example of a multiple-page memory array 301, which has N rows with 128 bytes per row, i.e. each row comprises an entire page of memory. N may be, for example, 128 for a total of 16 K-bytes of memory. A total of 128 column parity bytes (CP1 through CP128) and N page parity bits (P_0 through P_N) are calculated and stored. (Each column parity byte includes eight column parity bits. For example, column parity byte CP1 includes bits CP1_0 through CP1_7). The single array parity bit is denoted CP_P. The page parity bits, the column parity bytes and the array parity bit are all stored in RAM. Since only one page parity bit is provided for every 128 bytes of data, overhead is very low. For a 32 K-byte RAM, only 32 bytes of page parity bits are required (32 K-bytes/128 bytes=256 bits or 32 bytes) yielding an overhead of 0.10% (32 bytes/32 K-bytes*100). The column parity bytes consume another 128 bytes of memory yielding an overhead of 0.39% (128 bytes/32 K-bytes*100) for a total combined parity bit overhead of only 0.49%. This is substantially less than the 13.28% overhead required by the byte-based method described above, which employs one parity bit for every eights bits of data, and is dramatically less than the 62.5% overhead required by the conventional systems described above, which employ five parity bits for every eight bits of data.

Beginning at step 302, the microcontroller is activated to process electrical heart signals, identify pacing cycles, delivery therapy, and record diagnostic data. To this end, the microcontroller processes signals representative of intrinsic events such as P-waves, R-waves, T-waves and the like and, if needed, delivers pacing pulses in the form of A-pulses or V-pulses. The various intrinsic events and the various pacing pulses define a sequence of pacing cycles. For anti-bradycardia pacing, for example, the microcontroller may operate to ensure that the heart rate of the patient is always maintained at, at least, 80 beats per minute (bpm), by generating a pacing pulse whenever an intrinsic heart beat is not detected within a certain time window. For overdrive pacing to terminate a tachycardia, the microcontroller may operate, for example, to pace the heart at a rate five to ten bpm above the intrinsic tachycardia rate of the patient. In any case, the microcontroller monitors a sequence of successive heart cycles, which may be either intrinsic or artificial, with each heart cycle typically beginning with an intrinsic P-wave or A-pulse and ending with a resulting T-wave.

While performing these functions, the microcontroller frequently access the memory to either read data therefrom (such as control parameters) or to update data already stored (such as to record diagnostic data such as IEGM signals.) Each time data is written to the memory, the error detection and correction system, at step 304, automatically calculates and stores new page parity bits for each row containing data being updated. The error detection and correction system also calculates and stores new column parity and array parity bits for each memory array containing data being updated. Thus if the byte D256 of the third row of the page of memory of FIG. 8 is updated, parity bit P2, column parity byte CP1, and array parity bit CP_P are all recalculated. Data may be updated within various pages of the memory within each clock cycle requiring frequent updating of the various parity bits. No error detection or correction, however, is performed during the actual administration of therapy. Rather, during the period of time between successive pacing cycles, step 306 is performed to provide error detection and correction on one or more pages of memory, i.e. error detection and correction is performed following the detection of a T-wave of a current heart cycle and prior to the A-pulse or P-wave of the next heart cycle. In this manner, errors are detected and corrected within one or more pages of memory without affecting the delivery of therapy to the heart.

Depending upon the page size, array size and the total amount of memory, and on the speed of the microcontroller, the error detection and correction performed between pacing cycles may cover: one or more pages of memory (for example one 128 byte page); an entire memory array (for example one 16 K-byte array); or the entire memory of the device (for example one megabyte). If the error detection and correction system cannot examine all of the memory of the device in the time between two successive pacing cycles, then the error detection and correction system selects different portions of memory every pacing cycle, such that eventually all of the memory of the device is examined for errors. Preferably, the error detection and correction system keeps cycling through pages of memory to periodically achieve error detection and correction on the entire memory.

Figure 7:
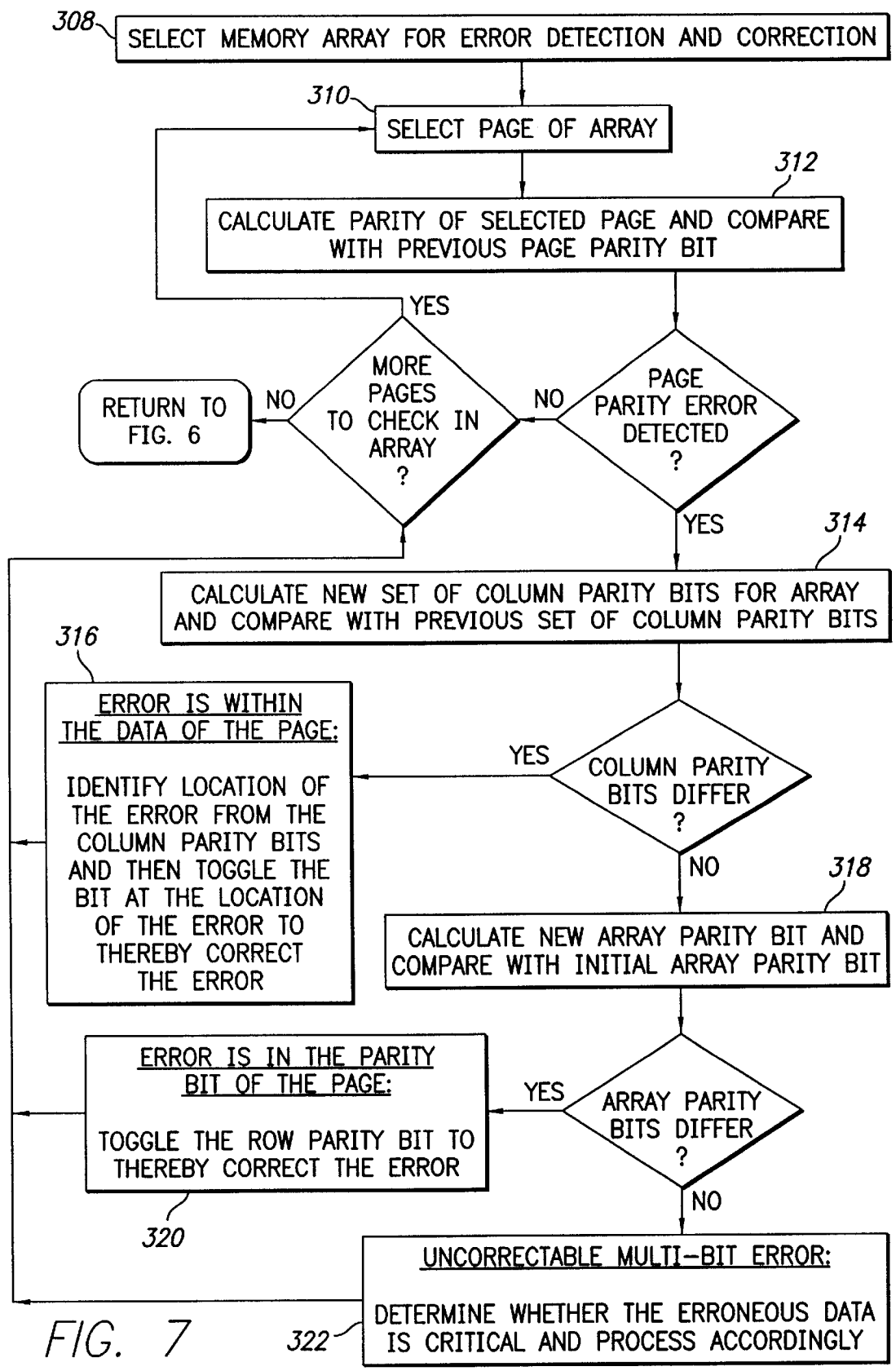
FIG. 7 is a flow chart illustrating details of the page-based error detection and correction method of FIG. 6.

Referring now to FIG. 7, the error detection and correction process performed at step 306 of FIG. 6 will now be described. At step 308, the error detection and correction system selects a memory array and then, at step 310, selects a page of the array for error detection and correction. The entire page comprises one row of the array. At step 312, the error detection and correction system calculates the parity of the page and compares the new page parity with the previously calculated and stored page parity. If the new page parity bit matches the stored page parity bit, then a single bit error has not occurred in the row and the next row is selected for processing at step 310. If, however, the new page parity bit does not match the stored page parity bit, then the error detection and correction system calculates a new set of column parity bits at step 314 (i.e. all 128*7 column parity bits of FIG. 8) and compares the new column parity bits with the column parity bits calculated and stored. If one of the new column parity bits differs from the stored column parity bits, then a single bit error has occurred in the data of the row and step 316 is performed to correct the error. The error is corrected by identifying the specific column parity bit that differs, then toggling the corresponding data bit of the row. In the example of FIG. 8, if new column parity bit CP128__7 differs from stored column parity bit CP128__7 for row 2 of the memory, the error is therefore at bit D255__1 and that bit is switched, i.e. if the bit is currently set to a 1, it is switched to a 0 and vice versa. Actual correction is preferably achieved by reading the entire row from memory, then XORing the row with the new column parity bits to thereby correct the error. Processing returns to step 310 to process other pages until there are no more pages in the array to examine, upon which processing returns to FIG. 6. If there is sufficient time before a next pacing cycle, additional memory arrays may be processed.

If, following step 314, the new column parity bits match the stored column parity bits, then either the error is in the page parity bit itself or a multiple bit error has occurred that cannot be corrected. To determine whether the page parity bit is in error, at step 318, a new array parity bit is calculated based on the new column parity bits and is compared against the initial array parity bit. If the array parity bits differ, then the error is in the page parity bit. If not, then a multiple bit error has occurred which cannot be corrected. In the example of FIG. 8, if new array parity bit CP__P differs from stored array parity bit CP__P based on an error initially detected in row 5, the error is therefore at bit P1 and that bit is switched, i.e. if the bit is currently set to a 1, it is switched to a 0 and vice versa. Actual correction is preferably achieved at step 320 by re-writing all of the data of the corrupted row, thereby triggering the hardware to automatically calculate and store a new page parity bit. Processing returns to step 310 to process other rows.

Following step 318, if the new array parity bit matches the stored array parity bit, then an uncorrectable multiple-bit error has occurred. In the example of FIG. 8, if an error has occurred both at bit location D128__0 within row P1 and at bit location D384__7 within row P3, the new and old column parity bytes will match and the new and old array parity bit will also match. In this case, it is not possible for the system to locate the two errors. At step 322, the system determines whether the data stored within the tested portion of memory is critical or not. As noted above, critical data may include control software whereas non-critical data may include diagnostic data. If not critical, the error may either be ignored or discarded. If the error is within memory storing control software, a back up therapy delivery control system is preferably activated until the control software can be re-installed.

In the following, a more detailed description of the error detection and correction techniques used in connection with the 8-bit RAM memory of FIG. 8 are provided. As noted, the hardware of the memory cannot detect an error. The software of the error detection and correction system operates as a background process to performs periodic checks on each row of RAM. Hence, error detection and correction is performed entirely in software. Software calculates the overall parity of all bits of a row by XORing all 8×128 or 1K bits (e.g. DO__7 through D127__0) and comparing the result to the page parity bit (e.g. P0). As noted, there is only one page parity bit for every 128 bytes of data. Upon detection of a parity error, the software stores the page address where the parity error occurred. The software then reads the contents of the entire 32 K RAM and calculates a column parity word of 1 K-bits (or 128 bytes) by XORing all 128 bytes and comparing the result to the column parity byte for the corresponding column. Addresses 0, 128, 256, . . . , 32640 generate the first column parity byte (CP1__7 through CP1__O); addresses 1, 129, 257, . . . , 32641 generate the second column parity byte (CP2__0 through CP2__7) . . . and addresses 127, 511, . . . , 32767 generate the 128th column parity byte (CP128__0 through CP128__7). By comparing the calculated column parity bytes and stored column parity bytes (via an XOR) the erroneous bit position is set to one. The software then determines the faulty address and bit position from the row and column parity error bytes and corrects the data before the next pacing cycle.

As a specific example of a single bit error correction, consider a case wherein the faulty address is 511, the correct data is 11001010, and the correct column parity for CP128__7 through CP128__0 is 10100101. If a single bit error occurs at bit position 5 (changing the data word to 11101010), the software detects the parity error then calculates the row and column parity bytes. The first calculated page parity byte differs from the stored value in bit position 3 (indicating a byte offset of 3*128=384). The value for CP128__7 through CP128__0 is thus calculated as 10000101. After XORing the calculated and stored bytes for column parities, the result for CP128__7 through CP128__0 is 00100000 (and 00000000 for all other column parity bytes), thus identifying bit position 5 of byte 127 as the erroneous bit. The erroneous address is calculated using the row byte offset (384) plus the column byte offset (127) yielding 511. By XORing the 00100000 byte calculated earlier with the current data in location 511 (11101010 XOR 00100000= 11001010) the data byte in address 24 is converted to its original value.

As noted, an advantage of the page-based method over the byte-based method discussed above is the lower overhead. A disadvantage is that the page-based method does not detected errors as data is read. Both methods, however, provide much lower overhead for error detection and correction than conventional systems and are very advantageous for devices such as pacemakers and ICDs. A particular advantage of the page-based technique is that it is implemented entirely software. Hence, error detection and correction can be provided in existing devices merely by installing new software into the device that incorporates the error detection and correction software module. In this manner, devices that do not currently employ error detection and correction can be easily upgraded, assuming the devices are configured to receive software upgrades and have sufficient memory to accommodate the additional error detection and correction software and memory.

Although described primarily with respect to pacemaker, aspects of the invention are applicable to other systems, such as systems employing other implantable medical devices. The exemplary embodiments of the invention described herein are merely illustrative of the invention and should not be construed as limiting the scope of the invention.

What is claimed is:

1. An implantable medical device comprising:
   a microcontroller operative to control operations of the device;
   a memory unit operative to store control software and data for use by the microcontroller;
   a hardware-based error detection unit operative to perform a parity check on a row of the memory; and
   a software-based single-bit error correction unit, operative in responsive to the detection of a parity error in a row of the memory, for correcting a single bit error within the row.

2. The device of claim 1 further including:
   row parity memory for storing an initial set of row parity bits, with each row parity bit associated with a respective row of the memory;

column parity memory for storing an initial set of column parity bits, with each column parity bit associated with a respective column of the memory; and page parity memory for storing an initial page parity bit associated with the entire set of column parity bits; and wherein the error detection unit performs the parity check on a row of the memory using the corresponding initial row parity bit; and wherein the error correction unit corrects a single bit error within data of the row using the initial set of column parity bits and corrects a single bit error within the parity bit associated with the row using both the initial set of column parity bits and the initial page parity bit.

3. The device of claim 2 for use with a memory wherein each row of the memory stores one byte and wherein the row parity bit associated with a respective byte is calculated by hardware.

4. The device of claim 3 wherein the error detection unit is a hardware unit comprising a set of exclusive-OR circuits, with each exclusive-OR circuit having its inputs coupled to the bit locations of a respective byte of the memory and having its output coupled to the respective hardware parity bit of the byte.

5. The device of claim 4 wherein the memory is hardwired to perform a parity check on data being read as it is read.

6. The device of claim 2 wherein the software-based error correction unit is operative to correct a single bit upset error, if any, occurring within a row by calculating a new set of column parity bits, comparing the new set of column parity bits with the initial set of column parity bits to determine the bit location of the error within the row, and then toggling the bit at the location of the error to thereby reset the bit to its correct value.

7. The device of claim 2 wherein the software-based error correction unit is operative to correct a single upset error, if any, occurring within the parity bit of the row by calculating a new set of column parity bits, comparing the new set of column parity bits with the initial set of column parity bits to verify that the error is within the parity bit of the row, and, if so, correcting the parity bit for the row.

8. The device of claim 7 for use with a memory wherein each row of the memory stores one byte and wherein the row parity bit associated with a respective byte is automatically generated by hardware upon writing of data into the byte of the memory and wherein the software-based error correction unit corrects the parity bit for the byte by re-writing the data into the byte thereby causing the byte of memory to automatically generate a corrected parity bit in the corresponding parity bit memory.

9. The device of claim 7 wherein the software-based error correction unit is also operative to detect a multiple-bit upset error, if any, within the row by calculating a new page parity bit based on the new set of column parity bits, comparing the new page parity bit with the initial page parity bit to detect any difference there-between, and, if no difference is detected, generating a signal indicative of an uncorrectable multiple-bit error.

10. In an implantable cardiac stimulation device having a microcontroller for controlling operations of the device and a memory unit for storing control software and data for use by the microcontroller, a method for performing error detection and correction comprising the steps of:

calculating and storing an initial set of row parity bits, with each row parity bit associated with a respective row of the memory;

calculating and storing an initial set of column parity bits, with each column parity bit associated with a respective column of the memory;

calculating and storing an initial page parity bit associated with the entire set of column parity bits;

performing a parity check on a row of the memory using the corresponding initial row parity bit; and responsive to the detection of a parity error in a row of the memory, correcting a single upset bit error, if any, within the row using the initial set of column parity bits and correcting a single upset bit error, if any, within the parity bit associated with the row using both the initial set of column parity bits and the initial page parity bit.

11. The error detection and correction method of claim 10 wherein the step of correcting a single upset data bit error, if any, within the row includes the steps of:

calculating a new set of column parity bits;

comparing the new set of column parity bits with the initial set of column parity bits to determine the location of the error within the data bits of the row; and toggling the data bit at the location of the error to thereby reset the data bit to its correct value.

12. The error detection and correction method of claim 10 wherein the step of correcting a single upset error, if any, within the parity bit includes the steps of:

calculating a new set of column parity bits;

comparing the new set of column parity bits with the initial set of column parity bits to verify that the error is within the parity bit of the row; and if so, correcting the parity bit for the row.

13. The error detection and correction method of claim 10 further including the step of detecting a multiple bit upset error, if any, within the row by:

calculating a new page parity bit based on the new set of column parity bits;

comparing the new page parity with the initial page parity to detect any difference there-between; and if no difference is detected, generating a signal indicative of an uncorrectable multiple bit error.

14. In an implantable cardiac stimulation device having a microcontroller for controlling operations of the device and a memory unit for storing control software and data for use by the microcontroller, a system for performing error detection and correction on the memory unit comprising:

means for calculating and storing initial row, column and page parity bits;

means for performing a parity check on a row of the memory using the corresponding initial row parity bit as the row of memory is being read by the microcontroller; and means, within the microcontroller, for correcting a single bit error, if any, within data of the row using the initial set of column parity bits and for correcting a single bit error, if any, within the parity bit associated with the row using both the initial set of column parity bits and the initial page parity bit.

15. The error detection and correction system of claim 14 wherein the means for correcting a single upset data bit error, if any, within the row includes:

means for calculating a new set of column parity bits;

means for comparing the new set of column parity bits with the initial set of column parity bits to determine the location of the error within the data bits of the row; and means for toggling the data bit at the location of the error to thereby reset the data bit to its correct value.

16. The error detection and correction system of claim 14 wherein the means for correcting a single upset error, if any, within the parity bit includes:

means for calculating a new set of column parity bits; and means for comparing the new set of column parity bits with the initial set of column parity bits to verify that the error is within the parity bit of the row, and, if so, for correcting the parity bit for the row.

17. The error detection and correction system of claim 14 further including the means for detecting a multiple bit upset error, if any, within the row.

18. The error detection and correction system of claim 17 wherein the means for detecting a multiple bit upset error, if any, within the row includes means for calculating a new page parity based on the new set of column parity bits; and means for comparing the new page parity with the initial page parity to detect any difference there-between, and, if no difference is detected, for generating a signal indicative of an uncorrectable multiple bit error.

19. In an implantable medical device having a microcontroller for controlling operations of the device and a memory unit for storing control software and data for use by the microcontroller, an error detection and correction system comprising:

row parity memory for storing an initial set of row parity bits, with each row parity bit associated with a respective row of the memory;

column parity memory for storing an initial set of column parity bits, with each column parity bit associated with a respective column of the memory;

page parity memory for storing an initial page parity bit associated with the entire set of column parity bits; and a hardware-based error detection unit for performing a parity check on a row of the memory using the corresponding initial row parity bit; and a software-based single-bit error correction unit, responsive to the detection of a parity error in a row of the memory, for correcting a single bit error within the row using the initial set of column parity bits and for correcting a single bit error within the parity bit associated with the row using both the initial set of column parity bits and the initial page parity bit.

\* \* \* \* \*